United States Patent [19]

Stroun et al.

[11] Patent Number: 5,952,170
[45] Date of Patent: Sep. 14, 1999

[54] METHOD FOR DIAGNOSING CANCERS

[76] Inventors: Maurice Stroun, 6, rue Pedro-Meylan, 1208 Geneve; Philippe Anker, 335, Rue de Bernex, 1233 Bernex, both of Switzerland; Valeri Vasioukhin, 320 N. Austin Blvd., ≠5, Oak Park, Ill. 60302

[21] Appl. No.: 08/663,230

[22] PCT Filed: Dec. 13, 1994

[86] PCT No.: PCT/IB94/00414

§ 371 Date: Jun. 17, 1996

§ 102(e) Date: Jun. 17, 1996

[87] PCT Pub. No.: WO95/16792

PCT Pub. Date: Jun. 22, 1995

[30] Foreign Application Priority Data

Dec. 16, 1993 [CH] Switzerland .............................. 3761/93

[51] Int. Cl.⁶ .............................. C12Q 1/68; C12P 19/34; C07H 21/04

[52] U.S. Cl. .......................... 435/6; 435/91.2; 536/24.31; 536/24.33

[58] Field of Search ..................... 435/6, 91.2; 536/23.1, 536/24.31, 24.33; 935/77, 78

[56] References Cited

U.S. PATENT DOCUMENTS

| | | | |
|---|---|---|---|
| 4,871,838 | 10/1989 | Bos et al. ................................. | 536/27 |
| 5,496,699 | 3/1996 | Sorenson ..................................... | 435/6 |
| 5,578,450 | 11/1996 | Thibodeau et al. ......................... | 435/6 |
| 5,602,243 | 2/1997 | Vogelstein ............................. | 536/24.3 |
| 5,693,470 | 12/1997 | de la Chapelle et al. .................. | 435/6 |
| 5,702,886 | 12/1997 | Volgelstein et al. ....................... | 435/6 |

FOREIGN PATENT DOCUMENTS

WO 93/22456  11/1993  WIPO .

OTHER PUBLICATIONS

Thibodeau et al. Microsatellite Instability in Cancer of the Proximal Colon, Science 260: 816–819, May 7, 1993.

Levenson et al. In PCR Protocols: A Guide to MEthods and Applications, Chapter 13, Eds, Innis et al., Academic Press, 1990.

Primary Examiner—Carla J. Myers
Attorney, Agent, or Firm—Young & Thompson

[57] ABSTRACT

A method of diagnosing and/or monitoring the development of cancer by analyzing the deoxyribonucleic acid (DNA) in blood plasma, and particularly by detecting any gene alterations in cancer cell DNA, e.g. oncogene mutations or deletions, tumour suppressor gene mutations or deletions, or microsatellite alterations.

6 Claims, No Drawings

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 24 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GACTGAATAT AAACTTGTGG TAGT                                              24

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CTATTGTTGG ATCATATTCG TCC                                               23

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ACTTGTGGTA GTTGGAGCTG G                                                 21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ACTTGTGGTA GTTGGAGCTG C                                                 21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACTTGTGGTA GTTGGAGCTG T                                                 21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:6:

ACTTGTGGTA GTTGGAGCTA                                                    20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ACTTGTGGTA GTTGGAGCTG A                                                  21

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACTTGTGGTA GTTGGAGCTT                                                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GACTGAGTAC AAACTGGTGG                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTCTATGGTG GGATCATATT                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTGGTGGTGG TTGGAGCAGA                                                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGTGGTGGTT GGAGCAGGTT                                              20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TCCGCGAAGT GATCCAGAAC                                              20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTTGGGGAGA CCCATTCTCA                                              20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AATCTGGGCG ACAAGAGTGA                                              20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

ACATCTCCCC TACCGCTATA                                              20

(2) INFORMATION FOR SEQ ID NO:17:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GTCAGTATTA CCCTGTTACC A                                              21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTTGAGGATT TTTGCATCAG T                                              21
```

METHOD FOR DIAGNOSING CANCERS

The present invention is concerned with a method for diagnosing and/or monitoring the evolution of various types of cancers after a chemotherapeutic treatment or after surgery.

It is well known that the diagnosis and the monitoring of the evolution of cancers is carried out, in addition to the observation and the direct examination of the tumors, by the analysis of biopsy samples, or in the case of blood cancers, an examination of the bone marrow. This implies either a surgical intervention, or an invasive operation of the biopsy type or further a bone medulla aspiration using a needle. Actually, in addition to the unpleasant if not dangerous nature of such methods to the patient, it was found that they could furthermore lack accuracy. In the case of certain leukemic diseases for example, the analysis of the sample of bone marrow taken has not made it possible to identify all the malignant clone varieties.

The purpose of this invention is hence to provide a method for diagnosing cancers which, on the one hand, is more accurate and more reliable and which, on the other hand, is easier to carry out without the need of resorting to invasive tests on the patients.

The method for diagnosing and/or monitoring the evolution of cancers, object of the invention and aimed at achieving the above purposes, includes the analysis of the deoxyribonucleic acid (DNA) contained in the blood plasma.

In fact, it has now been possible to demonstrate that patients suffering from different cancer diseases show increased amounts of DNA in the blood plasma. The method of diagnosis according to the invention is hence based on the detection of gene mutations in this plasma DNA, the blood plasma being a human material much more easily accessible that biopsy samples of tumors for example. Thus, oncogene mutations are frequently evidenced in numerous types of malignant tumors and, amongst them the mutations of the ras gene are particularly meaningful. However, the method can be applied to any gene modification of the DNA of the carcinomatous cells, such as mutations and deletions of the genes ras, APC, DCC, P53, etc of any oncogene or anti-oncogene gene (tumor suppressing gene) or furthermore modifications in the microsatellites. It has even been found that different mutations of the ras gene detected in the DNA of the blood plasma could be absent in the DNA of peripheral blood cells or in the case of certain patients suffering from leukemia in the DNA of bone marrow, which tends to confirm the greater reliability of the method according to the invention by comparison to known diagnostic methods.

Generally, the method of diagnosis according to the invention consists in extracting the DNA from blood plasma, in purifying and amplifying this DNA, and thereafter in determining gene mutations or deletions therein, in principle in a comparative test, with the blood plasma of a person presumed to be ill and that of another person in good health, as references.

The scope of the present invention extends to any technique for extracting, purifying or amplifying blood plasma DNA; also, any method appropriate for determining gene mutations can be used.

The diagnostic method according to the invention will now be described in more detail with reference to the two following examples:

EXAMPLE 1

Diagnosis of the cancer of the colon by detection of mutations of the K-ras gene.

In this first application of the method according to the invention, use was made of the determination of mutations in the codon 12 of the K-ras gene contained in the adenocarcinomata of the colon. These mutations occur generally upon transition from stage I adenoma to stage II adenoma, before the deletion or the mutation of gene P53, i. e. at a relatively early stage of the development of the tumor.

Blood samples (20–30 ml) were taken from 15 patients with a colo-rectal adenocarcinoma at different stages of development and heparinized, said patients having received at that time no anticancer drug. Thirteen of the 15 patients underwent subsequently surgery to remove the tumor; also, a total of approximately 400 ml of blood were taken from healthy persons, in order to isolate their plasma DNA.

The DNA was extracted from the tumors and from blood cells using well known conventional techniques.

As to the extraction of the DNA from blood plasma, it can be carried out as follows: the plasma is first subjected to a treatment using phenol, ether and chloroform. After dialysis against a SSC buffer (sodium chloride 0.15 M, trisodium citrate 0.015 M), the product is passed through a concanavallin A-Sepharose® column in order to eliminate the polysaccharides and then centrifuged in a $Cs_2SO_4$ gradient.

The DNA thus extracted and purified (10 to 100 ng) is then subjected to an amplification by PCR of the first exon of the K-ras gene in a volume of 100 µl.

The amplimers were

5'-GACTGAATATAAACTTGTGGTAGT-3' (SEQ ID NO:1) and

5'-CTATTGTTGGATCATATTCGTCC-3' (SEQ ID NO:2)

The amplifications were carried out in a buffer containing 50 mM of KCl, 10 mM of Tris-NaCl pH 0.3, 200 mM of each nucleotide, 1.8 mM of $MgCl_2$, 0.2 µM of each precursor and 2.5 units of "AmpliTaq"® DNA polymerase. 35 cycles were carried out for the DNA of the tumors and of the blood cells and 45 cycles for the DNA of the plasma (94° C. during 1 min, 59° C. during 1.5 min, 72° C. during 1 min, the last cycle being extended to 7 min at 72° C.).

Concerning the detection of the mutations, it can be carried out by any known appropriate method. In the present example, it was carried out by two different techniques for each sample tested.

(a) Hybridization of the PCR products with oligonucleotide probes which are mutation specific (according to Verlaan de Vries et al, Gene 50, 313–320, 1986):

The PCR products were placed in equal amounts on "Zeta-probe"® membranes (Bio-Rad, Hercules, Calif.) and hybridized with oligonucleotides specific for wild-type or mutant K-ras. The oligonucleotides were labelled with 32-P ddATP (Amersham GB). In order to separate the perfect hybrids from mismatches, the final washing of the membranes was carried out in a solution containing tetramethylammonium chloride 3 M, 50 mM of Tris-HCl at pH 8.0, 0.2 mM of EDTA and 0.1% of SDS, at 58° C. during 1 hour.

(b) Amplification by PCR with amplimers specific of point mutations or amplification by PCR for specific alleles (PASA) (according to Sommer et al, Biotechnique 12, 82–87, 1992):

In this method, which is more sensitive, the DNA is subjected to an amplification by PCR with amplimers complementary to the normal GLY sequences or the mutated ALA, VAL, SER, ASP or CYS sequences. These amplimers which are specific for the mutation have 3' terminations complementary to the mutations at the specific point. The enzyme Taq I polymerase (Perkin-Elmer Cetus, SWI) has no exonuclease activity at the 3' terminus and is therefore unable to amplify the DNA if the mismatch of a single base is located at the 3' terminus of the amplimer.

Each PCR was carried out in a volume of 40 µl of a solution containing 50 mM of KCl, 10 mM of Tris-HCl at pH 8.3, 2 mM of each nucleotide, 0.7 mM of MgCl$_2$, 0.2 mM of each precursor and 1 unit of "AmpliTaq"® DNA polymerase. Thirty five cycles were carried out (94° C. during 1 min, tempering at 55–62° C. during 2 min, extension at 72° C. during 1 min). The last cycle was extended to 7 min at 72° C. Each reaction was initiated by the "hot-start" technique. The amplimers used were the following:

5'-ACTTGTGGTAGTTGGAGCTGG-3' (SEQ ID NO:3) for the wild-type K-ras (renaturation at 55° C.), 5'-ACTTGTGGTAGTTGGAGCTGC-3' (SEQ ID NO:4) for the ALA 12 mutant (renaturation at 62° C.), 5'-ACTTGTGGTAGTTGGAGCTGT-3' (SEQ ID NO:5) for the VAL 12 mutant (renaturation at 61° C.), 5'-ACTTGTGGTAGTTGGAGCTA-3' (SEQ ID NO:6) for the mutant SER 12 (renaturation at 59° C.), 5'-ACTTGTGGTAGTTGGAGCTGA-3' (SEQ ID NO:7) for the mutant ASP 12 (renaturation at 60° C.), 5'-ACTTGTGGTAGTTGGAGCTT-3' (SEQ ID NO:8) for the CYS 12 mutant (renaturation at 59° C.) and in each case the anti sense amplimer 5'-CTATTGTTGGATCATATTCGTCC-3' (SEQ ID NO:2).

After amplification, the reaction products were analyzed by electrophoresis on a 0.8% polyacrylamide gel.

By using the first technique (a) described above, it was shown that it is not possible to demonstrate the same mutations in the DNA of the plasma as those detected in the DNA of the excised tumors (GLY to VAL, GYS to ALA); this technique seems to be applicable only if approximately 10% at least of the total DNA exhibits a point mutation. However, the above mutations could be identified in the plasma DNA with the second technique (b) described above; it appears that this technique enables the identification of mutations in a sample of plasma DNA mixed with a $10^4$ to $10^5$ excess of normal non-mutated DNA. On the other hand, with the same technique, it was not possible to detect the same mutations on the DNA samples from the blood cells.

Finally, all the control samples from healthy persons showed to be negative, i. e. exhibited no mutations of the plasma DNA.

EXAMPLE 2

Diagnosis of cancers caused by myeloid disorders, using the detection of mutations of the N-ras gene.

It is well known that a high incidence of N-ras mutations is observed in the DNA of bone marrow of patients affected by the myelodysplasia syndrome (MDS) or by acute myeloblastic leukemia (AML).

b 20 to 30 ml of blood were taken from ten patients affected by AML or MDS, this blood was collected on heparin and centrifuged on the "Ficoll Hipaque" gradient (Pharmacia, SWE). Also 400 ml of blood were taken from healthy persons. The interphase containing mononuclear cells was collected and used for extracting the DNA of the blood cells. The upper phase was centrifuged at 2500 G during 15 minutes and the supernatant was used for the extraction of plasma DNA. Furthermore, several samples of bone marrow from the same patients were taken for control analyses.

The DNA from the blood cells and from the bone marrow was isolated by treatment with protease K (Merck GER) in the presence of SDS, followed by a phenol extraction, a precipitation with ethanol and centrifugation in a Cs$_2$SO$_4$ gradient. The plasma DNA was extracted as described in example 1.

The DNA (10–100 ng) was amplified in a volume of 100 µl. The amplimers used (Oncogen Science, N.Y., USA) were 5'-GACTGAGTACAAACTGGTGG-3' (SEQ ID NO:9) and 5'-CTCTATGGTGGGATCATATT-3' (SEQ ID NO:10) for the first exon of the N-ras gene. The amplifications were carried out in an "Thermo-Cycler 480" (Perkin-Elmer Cetus, SWI) under the same conditions as those of example 1. Each cycle consisted of a denaturation step at 94° C. during 1 minute, a renaturation (at 51° C. for N-ras) during 1.5 minutes and an extension of one minute at 72° C., with a third extension segment of 5 seconds per cycle. The last cycle was followed by an extension of 7 minutes at 72° C. The products of the amplification (109 ng) were analyzed by electrophoresis on a 0.8% polyacrylamide gel.

The same two techniques of detection of mutations were employed as in example 1. In the second technique (b), the amplimer used for N-ras was 5'-CTGGTGGTGGTTGGAGCAGA-3' (SEQ ID NO:11) for the ASP 12 mutant, 5'-GGTGGTGGTTGGAGCAGGTT-3' (SEQ ID NO:12) for the CYS 13 mutant and 5'-CTCTATGGTGGGATCATATT-3' (SEQ ID NO:10) as the anti sense amplimer.

The results of the analyses obtained make it possible to confirm that the DNA of the diseased patients exhibited one or several mutations of the codon 12 (GLY to CYS or to ASP) or of the codon 13 (GLY to CYS) in the N-ras gene, while none of these mutations could be found neither in the DNA of the blood cells nor even in that of the bone marrow.

Thus, it is clearly apparent from the two illustrative examples above that the analysis of the DNA of blood plasma can provide a method for diagnosing and monitoring the evolution of a cancerous disease, which is more convenient, less traumatic (simply a sample of the patient's blood needs to be taken) and sometimes more reliable than known methods making use of biopsy samples.

We claim:

1. A method for diagnosing and/or monitoring progression of cancers, comprising extracting deoxyribonucleic acid (DNA) contained in a non-cellular blood fraction of a patient, purifying and amplifying the extracted DNA, and detecting microsatellite alterations in the amplified DNA, wherein the microsatellite alterations are indicative of the progression of a cancer in said patient.

2. A method according to claim 1, further comprising detecting oncogene mutations or oncogene deletions, or mutations or deletions of tumor suppressing genes occurring in the DNA of cancerous cells.

3. A method according to claim 2, in which the detection is applied to any oncogene, its fully complementary strand or tumor suppressing gene.

4. A method according to claim 1, in which the extracted DNA is amplified by PCR.

5. A method according to claim 4, in which the detection of gene mutations is carried out by hybridization of products obtained by PCR with oligonucleotide probes which hybridize specifically to the mutations.

6. A method according to claim 1, in which the detection of gene mutations is carried out by amplification by PCR and the use of primers which hybridize specifically to point mutations.

* * * * *